US006894778B2

(12) United States Patent
Palumbo et al.

(10) Patent No.: US 6,894,778 B2
(45) Date of Patent: May 17, 2005

(54) LOW DETECTION LIMIT TURBIDIMETER

(75) Inventors: Perry A. Palumbo, Fort Collins, CO (US); Paul D. Schlegel, Loveland, CO (US); Jeffrey M. Huhta, Loveland, CO (US); Richard P. Kolman, Loveland, CO (US)

(73) Assignee: Hach Company, Loveland, CO (US)

( * ) Notice: Subject to any disclaimer, the term of this patent is extended or adjusted under 35 U.S.C. 154(b) by 63 days.

(21) Appl. No.: 10/420,250

(22) Filed: Apr. 22, 2003

(65) Prior Publication Data

US 2003/0214653 A1 Nov. 20, 2003

Related U.S. Application Data

(60) Provisional application No. 60/375,342, filed on Apr. 23, 2002.

(51) Int. Cl.$^7$ .............................................. G01N 21/00
(52) U.S. Cl. ...................................................... 356/338
(58) Field of Search ................................ 356/335–343; 250/574, 576

(56) References Cited

U.S. PATENT DOCUMENTS

| | | | | | |
|---|---|---|---|---|---|
| 4,017,190 A | * | 4/1977 | Fischel | ........................ | 356/40 |
| 4,319,138 A | * | 3/1982 | Sweet | ........................ | 250/578 |
| 4,343,552 A | * | 8/1982 | Blades | ........................ | 356/339 |
| 5,872,361 A | * | 2/1999 | Paoli et al. | .............. | 250/341.8 |
| 6,003,362 A | * | 12/1999 | Dieckmann et al. | ....... | 73/19.12 |
| 6,307,630 B1 | * | 10/2001 | Banerjee | ..................... | 356/436 |

* cited by examiner

Primary Examiner—Michael P. Stafira
(74) Attorney, Agent, or Firm—Dean P. Edmundson

(57) ABSTRACT

A turbidimeter having an arrangement of internal surfaces, optical surfaces, and optical restrictions to the field of view of both the illumination and the detector means to significantly improve the lower detection limit of the turbidimeter by reducing the detected signal due to stray light.

19 Claims, 2 Drawing Sheets

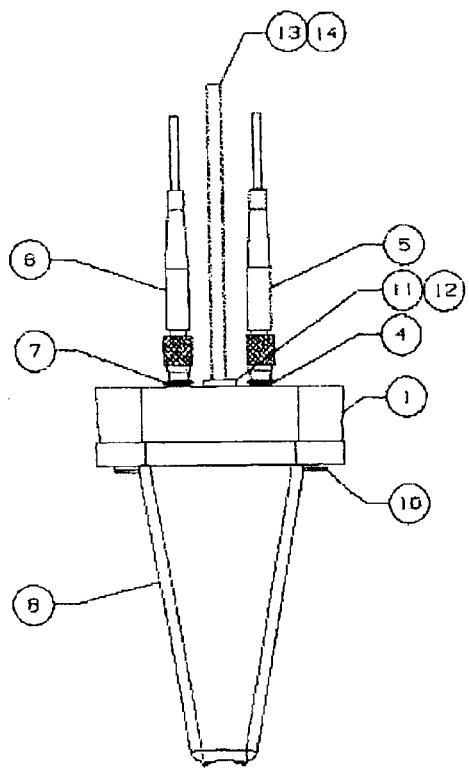
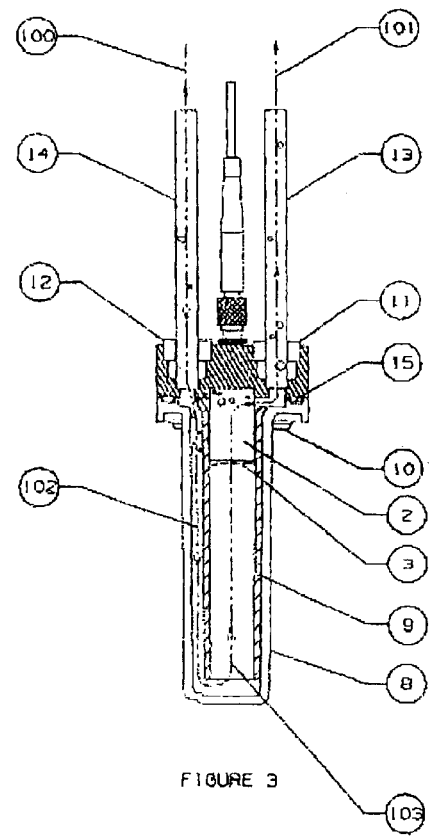
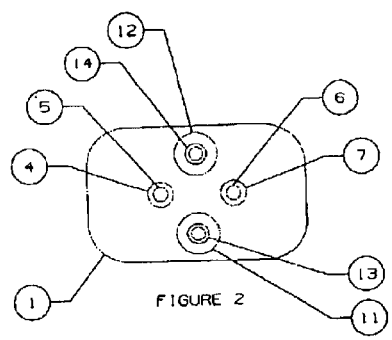

LOW DETECTION LIMIT TURBIDIMETER

CROSS-REFERENCE TO RELATED APPLICATION

This application is based upon, and claims the benefit of, our Provisional Application No. 60/375,342, filed Apr. 23, 2002.

FIELD OF THE INVENTION

This invention relates to turbidity measurement of solids in a suspension. More particularly, it relates to determination of the concentration of solids in suspension by detection of scattered light caused by the suspended solids.

BACKGROUND OF THE INVENTION

A problem exists in the measure of solids or particles in suspension when the concentration of such particles is low and the size of the particles is small (e.g. 0.05 to 2 µm) in size, as in the detection of an integrity fault or "breakthrough" in the micro-filtration process of drinking water. A typical filter or cartridge used in micro-filtration is composed of a plethora of individual fibers through which the unfiltered or "unfinished" water is passed. In order to assess the integrity of the filter, the effluent water of the filtering process is monitored in comparison to an established limit of turbidity in drinking water.

It is desirable that the turbidimeter be of low volume so that response to a change in the amount of solids in the effluent is rapid and that sample volume used for monitoring purposes is insignificantly small in comparison to the volume of filtered suspension. Another desirable attribute of a turbidimeter is an ability to generate a detectable change in signal due to an incremental corresponding change in the amount of solids in the suspension. A conventional turbidimeter cannot achieve these requirements.

A conventional turbidimeter measures the concentration of solids in suspension by means of projecting a beam of light through a medium and measuring the amount of light scattered by the suspended solids. The lower limit of detection of this method is determined by the self-generated signal of the detector means. A conventional turbidimeter can approach the lowest limit of detection only when the amount of light that reaches the detection means not due to light scattered from the suspended solids is sufficiently reduced to below that of the self-generated signal of the detector means or noise level of the detector. Light that reaches the detector and generates a signal not associated with solids in the suspension medium is stray light. A signal generated by the detector due to stray light is not distinguishable from the signal which is caused by the suspended solids, thus the lower limit of detection is increased to a level greater than that caused by stray light.

As the volume of a conventional turbidimeter is reduced, the signal level of the detection means due to stray light increases due to diffuse reflections of the internal surfaces and air bubbles both in suspension and on the internal surfaces of the turbidimeter. Stray light that is diffusely reflected from internal surfaces is caused by imperfection in the quality of the surfaces and/or by the presence of air bubbles or other particles that form or adhere to the internal surfaces. Diffusely reflected light can illuminate other internal surfaces. When an internal surface is illuminated by direct or non-direct means and that surface falls within the field of view of the detector means, a signal is generated that increases the detection limit of the turbidimeter making it insensitive to small changes in the turbidity of the suspension. Air bubbles present in the suspension media have a similar effect in increasing the detection limit by diffusely reflecting and refracting light within the internal volume of the turbidimeter. Air bubbles efficiently refract and reflect light in all directions due to the spherical nature of the air bubble and due to differences of the refractive index of air and the refractive index of the suspension media in which the bubbles reside.

Another cause of poor detection of solids in suspension is illumination of the sample that is unequal to the volume of the sample that falls within the field of view of the detector. Illumination that falls outside of the field of view of the detector does not contribute to the signal generated from the solids in the suspension, and the signal level is decreased due to loss in irradiance of the sample. If the field of view of the detector is greater than the volume of the sample illuminated by the source beam, an increased susceptibility to stray light will ensue.

The turbidimeter of the present invention incorporates a novel arrangement of internal surfaces, optical surfaces, and optical restrictions to the field of view of both illumination and detection means to significantly improve the lower detection limit of a turbidimeter by reducing the detected signal not due to solids in suspension.

SUMMARY OF THE INVENTION

The present invention overcomes the problem of poor detection limit in the measure of turbidity of a suspension.

In one embodiment, light generated by a source is collimated, or nearly so, by means of a collimating lens and then emitted through the suspension to be measured. The field of the source beam and beam diameter are controlled by the distance of the source from the collimating lens and by the diameter of the source and the collimating lens and optical power of the collimating lens. An equivalent field is imposed on the detector means such that the field of the detector means and field of the source beam coincide at the position of the field stop. The angle separation between the two fields is selected based upon the physical properties of the suspended solids to be measured, such as size of the particles in suspension. Typically 90 degrees is used in the measure of turbidity, as this angle provides a signal least dependent on the size of the particles in suspension. Other angles can be used to advantage, such as 40 or 50 degrees relative to the source beam, to provide a greater sensitivity to the smaller particles in suspension or to increase the path length of detection or overlap between the source beam and the detector field.

In another embodiment, the source beam and the detector means are each oriented at an angle of about 22 degrees relative to the vertical centerline of the enclosure 8 (as shown in FIG. 6) so that no prisms are required to be used in the turbidimeter assembly. The source beam and the detector field of view intersect near the center of the enclosure 8.

Ideally the source beam is completely extinguished beyond the field of view of the detector, and the detector field of view extends only to the intersection of the source beam and detector field of view and not beyond. In practice, the source beam and the detector field of view interact not only at an area of intersecting fields but also with the internal surfaces of the turbidimeter. Arrangement of the internal surfaces of the turbidimeter within the field of the detector and emitted beam can be used to the advantage of providing light traps for both fields. The light trap for the emitted beam serves to contain internal reflection to within the light trap area and effectively extinguish the beam from radiating as stray light into the field of view of the detector. A light trap may also be provided for the detector field of view to prevent the detector field from extending beyond the light trap area as would otherwise occur from specular reflection of a single interior surface. Thus stray light is effectively reduced for a small volume turbidimeter through extinction of the emitted beam and trapping of the detector field.

The problem of air bubbles both in suspension and on internal surfaces are effectively mitigated by providing internal surfaces absent of nucleation sites, removal of bubbles prior to entering the sensing area of the turbidimeter, and by providing a sample flow path that sweeps the interior surfaces of the turbidimeter. The sample enters the turbidimeter through the inlet port. Air bubbles are removed from the suspension by providing a chamber on the inlet of the turbidimeter wherein the velocity of the sample flow is reduced allowing the bubbles to separate from the suspension by means of buoyancy. The bubbles that collect at the top of the inlet chamber, or bubble trap, are provided a means of escape through the outlet port of the turbidimeter along with the measured sample suspension. The sample flow, free of suspended bubbles, enters the sensing volume of the turbidimeter through sampling ports in the light traps located at the bottom of the turbidimeter. Both light traps taper from the sampling ports and open out to include the sensing area of the turbidimeter and outlet port. The velocity of the flow increases as the sample passes from the bubble trap area of the turbidimeter into the light trap area, then reduces as the light trap area opens into the sensing volume. The increased velocity of flow in the light trap area maintains the surfaces of the light traps in a condition free of bubbles, solids or sediments that would otherwise impair detection of solids in suspension due to an increase in stray light.

BRIEF DESCRIPTION OF THE DRAWINGS

FIG. 1 is a side elevational view of one embodiment of the turbidimeter of the invention;

FIG. 2 is a view of the connection end of the turbidimeter of FIG. 1 showing the sample flow inlet and outlet connections and, also, the emitting and detecting fiber optic connections;

FIG. 3 is a sectional view showing the liquid sample flow path;

DETAILED DESCRIPTION OF THE INVENTION

Figure 4:
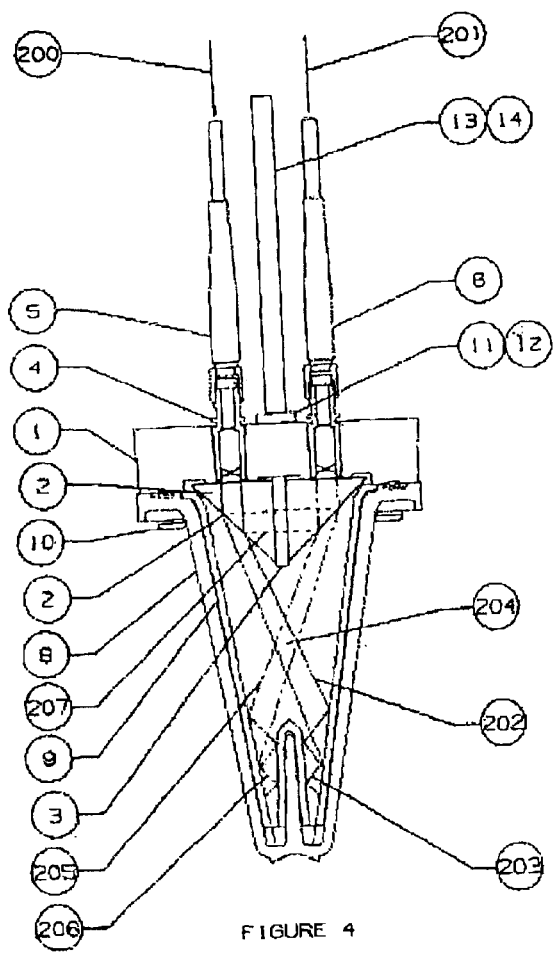
FIG. 4 is a sectional view showing the optical ray path in the sample chamber.
Figure 5:
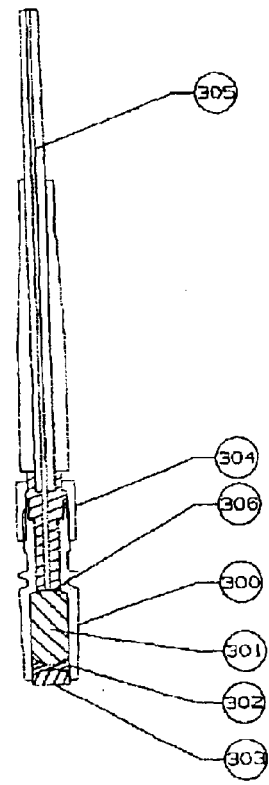
FIG. 5 is a sectional view showing a solid glass fiber optic collimating lens assembly and fiber optic terminator.

One embodiment of the present invention is shown in FIGS. 1–5, comprising an optical base 1, right angle prisms 2, optical filter 3, collimate lens assembly 4, focus lens assembly 7 and fiber optic cable assemblies 5 and 6. An outer enclosures, flow diverter 9, retaining screws 10, tubing connectors 11 and 12, sample inlet tube 14, sample outlet tube 13, and gasket 15 comprise the remaining components of this embodiment of turbidimeter.

The optical base 1 provides a means to align and position the prisms 2, optical filter 3, and collimating lens assemblies 4 and 7. The right angle prisms 2 and optical filter 3 are bonded together using optical epoxy such as "Epo-Tek 301-2" and attached to the optical base 1 using structural epoxy such as "3M Scotch-Weld 2216 B/A". The optical filter 3 extends beyond the face of the prisms to prevent stray light from being scattered into the return path 201 in FIG. 4. The collimating lens assemblies are bonded in like fashion to the prisms 2 and optical base 1 using the optical and structural epoxies previously described. Tubing connectors 11 and 12 are press fit into the optical base and provide a means to connect the sample inlet and outlet tubing 13 and 14 to the inlet and outlet ports of the turbidimeter assembly.

The flow diverter 9 and gasket 15 are captured between the outer enclosure 8 and the optical base 1, held together by retaining screws 10. Retaining screws 10 on the outside surface of outer enclosure 8 provide a means to service the turbidimeter while the turbidimeter is mounted to a bulkhead or raceway without disturbing inlet and outlet tubing 13 and 14 nor disturbing the fiber optic cable assemblies 5 and 6. Service can include the replacement of the flow diverter due to chemical damage or the removal of sediments that may accumulate during catastrophic events beyond the design intent.

Light emitted by a suitable source such as a laser diode is coupled to an optical fiber assembly 5 of FIG. 4 and transmitted to the turbidimeter assembly. Collimate lens assembly 4 modifies and restricts the angular field of the emitted light exiting the optical fiber assembly 5 to create source beam 202. Similarly, focus lens assembly 7 controls the field of view 205 of the fiber optic assembly 6 used to transmit scattered light to a detection means such as a photomultiplier tube. Both lens assemblies 4 and 7 can in fact be of the same construction as in FIG. 5. A desirable attribute of both the collimate and focus lens 4 and 7 is that environmental effects such as condensation of water will not cause an enlargement of the field of view of either lens due to the scatter of light by condensing moisture. This problem is overcome in the present invention by the elimination of all glass-air interfaces. Optical fiber 305 of fiber optic assemblies 5 and 6 are held against a triplet formed by lens elements 301, 302 and 303 via retaining nut 304 of the fiber optic assembly and lens housing 300. This triplet is bonded together using a suitable optical adhesive such as "Norland Products No. 61". A silicone RTV such as "GE TSE399-B" may be used to bond the triplet assembly to the lens housing 300. Air is eliminated from the fiber-triplet interface by the application of a thin film of silicon optical grease 306 such as "Bicron BC-630". Curvature, thickness and material of lens elements 301, 302 and 303 are judiciously selected by one skilled in the art to obtain a beam with the desired field properties and diameter.

The angular separation of source beam 202 and detection field of view 205 is provided, in one embodiment, by means of right angle prisms 2 of refractive index higher than that of the suspension medium (e.g. water) and the incident angle of the source beam and detection field of view. The collimate lens 4 and focus lens 5 are separated by an equal distance from the centerline of optical filter 3. The angle of incidence between the suspension and prisms 2 is preferentially selected to be 45 degrees and thus creates a second internal optical path 207 through the prisms 2 and optical filter 3 independent of the suspension being tested. This is accomplished by means of specular reflection at the interface between the suspension and prism surfaces. The second internal optical path 207 permits discrimination of the returned light by wavelength and/or by the presence or absence of the suspension medium. Selection of an appropriate filter material, such as "Schott Glass Technologies RG-850 or RG-1000", or by means of interference coatings, the optical filter 3 can block or transmit the specular reflected light depending upon the source wavelength of light. Additionally, when the index of refraction of the prisms is sufficiently large and the suspension medium is not present, all of the light of the source beam 202 is totally internally reflected through the optical filter to the lens assembly 7.

Internal optical path 207, which is a result of the selective transmission of light through optical filter 3, can be used to several advantages. One advantage of the internal optical path is in the detection of surface contamination at the interface between the prisms 2 and the suspension. As the surfaces of the prisms 2 are contaminated, a baseline change in the internally transmitted signal is observed and the appropriate action can then be taken such as cleaning of the surfaces. Another use of the internal optical path 207 is as a check of the integrity of the optical cables 5 and 6 by observing the response of the detection means to a change in transmitted signal. The internal optical path 207 can also be used to reference the response of the detection means independent of the suspension in which the prisms 2 are immersed. To independently reference the detector response, the signal generated by the suspension must be significantly less than the response generated by the transmission light along internal optical path 207, or said response due to the suspension is subtracted from the response due to the internal optical path 207. An observation made through the internal optical path 207 is compared to a previous observation of same said optical path at known source intensities of both observations. Fiber optic cable movement or the accumulation of debris on the internal surfaces of the turbidimeter or changes in the system response are examples for which an internal intensity change is observed. The ratio change of the internal observations, or reference measurements, applied to observations made through the suspension at a wavelength not transmitted through the internal optical path 207 provides the means to correct the observations for changes not due to changes in the suspension.

Figure 6:
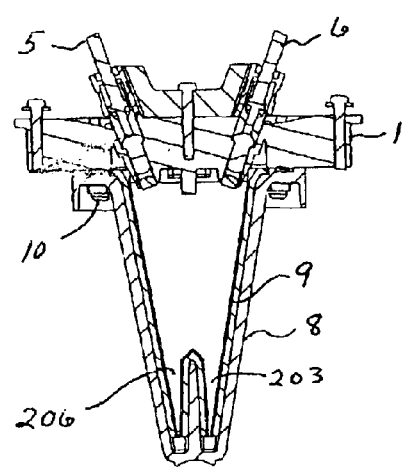
FIG. 6 is a sectional view showing another embodiment of turbidimeter of the invention.

Source beam 202 is refracted at the interface of the suspension and the prism 2. The angle of refraction of the source beam 202 is determined by the angle of incidence of the interface and the difference of refractive indices of the prism and the suspension per the law of refraction, "Snell's law", as n(sin(i))=n'(sin(r)), where "n" is the refractive index of one medium and "n'" is the index of refraction of a second medium, "i" is the incident angle and "r" is the refracted angle. For water as a suspension medium, and Schott Optical Glass SF-10 as the prism material, the resulting angle of refraction is approximately 20.885 degrees at 670 nm. Both source beam 202 and detection field of view 205 are refracted in like fashion to intersect at a distance based upon the separation of collimate lens assembly 4 and focus lens assembly 7 and the thickness of the prism in which the beams propagate. Alternately, the prisms 2 and optical filter 3 may be eliminated and the collimate lens 4 and focus lens 7 may be positioned along the path of refraction at said 20.885 degrees and obtain a low detection limit turbidimeter without an internal optical path 207. This is illustrated in the sectional view of FIG. 6.

The angle of the source beam 202 and the field of view 205 may vary, so long as the source beam and the field of view intersect in the suspension (preferably near the center of the enclosure 8), as shown in FIG. 4. The angle of intersection may vary (e.g. from about 5 to 175 degrees), although for many purposes it is preferred to be in the range of about 40 to 50 degrees. Different angles may be used based upon the scatter characteristics of the suspension (i.e. different angles will be sensitive to different attributes of the scattering medium).

Particles in suspension within the field of view 205 of the detection means that reflect light from the source beam 202 contribute to a detectable signal. The overlapping fields of view, a result of the refraction of the source beam 202 and detection field of view 205 by prisms 2, define the sensing area 204 of the turbidimeter. Sensing volume 204 defines the imaginary spatial position of the optical stop for the optical design of collimate lens assembly 4 and focus lens assembly 7 to provide the best transfer of energy. Light from source beam 202 which does not interact with particles within the sensing volume 204 continues to propagate along the path defined by collimate lens assembly 4 to the absorption of beam energy within light trap area 203 of flow diverter 9. Likewise, the field of view 205 of focus lens assembly 7 views into a similar light trap structure 206 on the opposite wall of the flow diverter 9. Light traps 203 and 206 provide attenuation of energy by multiple reflection of the specular component of the optical beams 202 and 205 incident on the light absorbing walls of the light trap areas. The light absorption characteristic of the material used for flow diverter 9 of light traps 203 and 206, such as "Filtron E800" (e.g. an acrylic or polymethyl methacrylate plastic which is dyed) provides the means for the attenuation of the optical energy. A quality optical finish, as defined by MIL-O-13830 as 80–50 scratch and dig, of the inside surface of flow diverter 9 contributes to proper attenuation of the optical beams without scattering light to within the field of view 205 of focus lens assembly 7. The quality optical finish also eliminates nucleation sites within light trap areas 203 and 206, and provides surfaces that can be maintained free of particle accumulation by the flow of the sample across said surfaces.

Preferably the chamber enclosure 8 is tapered from the top to the bottom, as shown and illustrated in the drawings. Preferably there also are two light traps 203 and 206 in the lower portion of the enclosure 8, as illustrated. Preferably each of these light traps is also tapered vertically, as shown, so that they are wider at the top than at the bottom. The purpose of the light traps is to attenuate or absorb light which enters into them so that scattered or stray light (not resulting from interaction of the source beam with particles in the field of view 205) will not enter into the field of view 205. The presence of tapered, light-absorbing walls in the light traps assures that stray light will not be reflected out from the traps. The geometry and depth of the light traps may vary.

Optical base 1, outer enclosure 8, flow diverter 9, and gasket 15 combine to form a unique flow path for the suspension, e.g. water. The flow path removes air bubbles from the suspension prior to reaching sensing volume 204 and provides a velocity change in the sample flow to facilitate the removal of air bubbles and prevent particles from accumulating on the internal surfaces of the turbidimeter. The sample flow 100 is carried to the turbidimeter by inlet tube 14 and enters the turbidimeter via tubing connector 12 into the optical base 1. The sample flow 100 follows a path through optical base 1 where it is primarily diverted into an area of low flow velocity 102 formed between flow diverter 9 and outer enclosure 8. The flow velocity in this area is a result of an increase in volume along the flow path formed between the flow diverter 9 and the outer enclosure 8, which may possess substantially different cross-sectional dimensions. Low flow velocity area 102 facilitates the removal of air bubbles by the natural buoyancy of the bubbles in the suspension. Air bubbles separated from the suspension in the area of low flow velocity 102 accumulate at the optical base oriented above area of low flow velocity 102. A portion of the sample that does not enter the bubble trap 102 is diverted to follow a direct path to outlet connector 11 to outlet tube 13. The direct path to outlet connector 11 provides a means to remove the accumulation of air at optical base 1 through outlet connector 11 and outlet tube 13. The suspension, free of air bubbles, enters an area of high velocity 103 formed by a restriction at the apex of the light traps 203 and 206 through which the liquid flow enters the sensing volume 204. The increase in flow velocity facilitates the removal of particles and air bubbles that may form on the interior walls of the diverter or light traps 203 and 206, maintaining surfaces that do not scatter light into the detection field of view 205. The measured flow 101 exits the turbidimeter through an exit port in optical base 1 through exit connector 11 and is carried from the turbidimeter via sample outlet tube 13.

A turbidimeter in accordance with the present invention achieves low detection limit by use of a novel arrangement of corresponding optical fields of emission and detection. Also included is a novel arrangement of light traps that do not harbor contaminates or nucleation sites. A unique liquid flow path that removes suspended air bubbles from the suspension is also included which maintains the integrity of the internal surfaces of the turbidimeter free from accumulation of air bubbles and contaminates.

The embodiments described herein may be accomplished in a variety of forms without departing from the scope or intent of this invention by those skilled in the art and the invention is not limited to the disclosed embodiments.

What is claimed is:

1. A turbidimeter for measuring the turbidity of a liquid containing particles, comprising:
   (a) sample receiving chamber means having inlet and outlet means for liquid sample ingress into said chamber means and egress therefrom;
   (b) light source means for projecting a light beam into said chamber means; wherein said light source means further comprises a collimating lens for collimating said light beam; wherein said light source means is free of surfaces on which condensation may occur;
   (c) detector means for detecting light scattered by said particles in said liquid sample in said chamber means; wherein said detector means has a field of view which intersects said light beam in said chamber means; wherein said detector means further comprises focus means for focusing said light scattered by said particles in said field of view; wherein said focus means is free of surfaces on which condensation may occur; and
   (d) first and second light trap means for trapping said light beam and preventing; wherein said first light trap means prevents said light beam from radiating to said detector means as stray light; and wherein said second light trap means prevents the detector field from extending beyond said second light trap.

2. The turbidimeter in accordance with claim 1, further comprising refracting means between said light source and said liquid sample.

3. The turbidimeter in accordance with claim 2, wherein said refracting means comprises a prism.

4. The turbidimeter in accordance with claim 1, further comprising refracting means between said detector means and said liquid sample.

5. The turbidimeter in accordance with claim 4, wherein said refracting means comprises a prism.

6. The turbidimeter in accordance with claim 1, wherein said chamber means further comprises a bubble trap for removing bubbles present in said liquid sample.

7. The turbidimeter in accordance with claim 1, wherein said chamber means includes an interior surface, and wherein said chamber means further comprises a flow diverter which defines a volume between said interior surface of said chamber means and said flow diverter; wherein said light trap means includes a lower end having an opening therethrough; wherein said diverter causes said liquid to flow downwardly through said volume at low flow velocity after which said liquid flows upwardly through said opening at a flow velocity greater than said low flow velocity.

8. The turbidimeter in accordance with claim 1, wherein said light trap means comprises surfaces which are light absorbing.

9. The turbidimeter in accordance with claim 1, further comprising base means; wherein said chamber means is detachable from said base means.

10. The turbidimeter in accordance with claim 9, wherein said light source means and said detector means are supported by said base means.

11. The turbidimeter in accordance with claim 10, wherein said inlet and outlet means comprise tubes which extend through, and are supported by, said base means.

12. A turbidimeter for measuring the turbidity of a liquid containing particles, comprising:
   (a) chamber means having inlet and outlet means for liquid ingress into said chamber means and egress therefrom; wherein said chamber means includes an interior surface; wherein said chamber means further comprises a flow diverter which defines a volume between said interior surface and said flow diverter; and wherein said chamber means further comprises a bubble trap for removing bubbles present in said liquid; wherein said diverter causes said liquid to flow downwardly through said volume at low flow velocity before said liquid is able to flow upwardly at higher flow velocity;
   (b) light source means for projecting a collimated light beam into said chamber means;
   (c) detector means for detecting light scattered by said particles in said liquid in said chamber means; wherein said detector means comprises focus means and has a field of view which intersects said light beam in said chamber means to define a sensing volume;
   (d) first light trap means for trapping said light beam and preventing said light beam from radiating to said detector means as stray light; and second light trap means for preventing the field of view of said detector means from extending beyond said second light trap; wherein each said light trap means includes at least two non-parallel light absorbing surfaces; wherein said first light trap means includes a lower end having an opening through which said liquid flows upwardly at said higher velocity after leaving said diverter.

13. The turbidimeter in accordance with claim 12, wherein said light source means and said detector means are free of surfaces on which condensation may occur.

14. The turbidimeter in accordance with claim 12, wherein each said light trap means is tapered from a narrow lower end to a wider upper end.

15. The turbidimeter in accordance with claim 12, further comprising an optical filter positioned between light source and said detector means; wherein said optical filter is opaque to wavelengths of light which are used to measure turbidity of said liquid.

16. The turbidimeter in accordance with claim 12, further comprising first refracting means between said light source and said liquid and second refracting means between said detector means and said liquid.

17. The turbidimeter in accordance with claim 16, wherein each said refracting means comprises a prism.

18. The turbidimeter in accordance with claim 12, wherein said second light trap means includes a lower end having an opening through which said liquid flows upwardly after leaving said diverter.

19. A method for correcting a turbidity measurement of a liquid containing particles, comprising the steps of:

(a) providing a turbidimeter comprising a sample receiving chamber, collimated light source means, detector means including focus means for focusing light scattered by said particles in said liquid, first refracting means between said light source and said liquid and second refracting means between said detector means and said liquid, and an optical filter between said first and second refracting means which is opaque to the wavelength of light used to measure the turbidity of said liquid;

(b) irradiating said liquid in said chamber with light of a first wavelength from said light source and detecting a first signal with said detector means;

(c) directing light of a second wavelength from said light source through said optical filter and detecting a second signal;

(d) correcting said first signal in response to the difference between said first and second signals to obtain the measurement of turbidity of said liquid.

* * * * *